(12) United States Patent
Li et al.

(10) Patent No.: US 9,200,305 B2
(45) Date of Patent: Dec. 1, 2015

(54) GENERATION OF ENGINEERED MOLECULAR WEIGHT STANDARDS

(75) Inventors: Lei Li, San Francisco, CA (US); Dennis Yee, Hercules, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 13/331,946

(22) Filed: Dec. 20, 2011

(65) Prior Publication Data

US 2013/0153419 A1 Jun. 20, 2013

(51) Int. Cl.
| | |
|---|---|
| *C12P 21/00* | (2006.01) |
| *C07K 1/26* | (2006.01) |
| *C09K 3/00* | (2006.01) |
| *C07K 2/00* | (2006.01) |
| *C07K 14/00* | (2006.01) |
| *C12P 21/02* | (2006.01) |

(52) U.S. Cl.
CPC ..................................... *C12P 21/02* (2013.01)

(58) Field of Classification Search
None
See application file for complete search history.

(56) References Cited

U.S. PATENT DOCUMENTS

| | | | | |
|---|---|---|---|---|
| 5,449,758 | A | * | 9/1995 | Hartley .......................... 530/350 |
| 6,001,604 | A | * | 12/1999 | Hartman et al. .............. 435/69.4 |
| 2009/0087873 | A1 | | 4/2009 | Bogoev et al. |
| 2010/0022455 | A1 | | 1/2010 | Chilkoti |

FOREIGN PATENT DOCUMENTS

| | | |
|---|---|---|
| WO | 2006/031611 A1 | 3/2006 |
| WO | 2010/003193 A1 | 1/2010 |

OTHER PUBLICATIONS

Terranova et al. Neuroscience Letters. 213;79-82:1996.*
Hrobowski et al. Virology. 2(49):2005.*
Li et al. Biochemical and Biophysical Research Communications. 352;932-935:2007.*
International Search Report and Written Opinion dated Mar. 11, 2013 for International Patent Application No. PCT/US2012/70364, 13 pages.

* cited by examiner

*Primary Examiner* — Amber D Steele
*Assistant Examiner* — Schuyler Milton
(74) *Attorney, Agent, or Firm* — Kilpatrick Townsend & Stockton LLP

(57) ABSTRACT

The invention provides methods of generating physical analog polypeptides, and polypeptides generated employing the methods of the invention, that have the same amino acid composition of a reference protein, but have an unrelated primary sequence. The invention further provides compositions and methods employing such proteins.

10 Claims, 7 Drawing Sheets

FIG. 1

GENERATION OF ENGINEERED MOLECULAR WEIGHT STANDARDS

REFERENCE TO A "SEQUENCE LISTING," A TABLE, OR A COMPUTER PROGRAM LISTING APPENDIX SUBMITTED AS AN ASCII TEXT FILE

The Sequence Listing written in file -867-1.TXT, created on Feb. 14, 2012, 16,384 bytes, machine format IBM-PC, MS-Windows operating system, is hereby incorporated by reference in its entirety for all purposes.

BACKGROUND OF THE INVENTION

Protein molecular weight reference standards are widely used in applications, such as electrophoresis or chromatography, where it is desirable to determine the characteristics of a protein. This application provides new protein reference standards, e.g., that have a new sequence, but retain the physical properties of other used reference markers.

BRIEF SUMMARY OF THE INVENTION

The invention is based, in part, on the surprising discovery that new recombinant proteins can be generated that do not retain the amino acid sequence or functional activity of a reference protein, but conserve the physical properties (e.g., molecular weight, isoelectric point, charge, electrophoretic migration, chromatographic characteristics) of the protein. Such proteins can be used, for example, as a protein reference standard, e.g., for use in determining the molecular weight of another protein of interest.

Thus, in one aspect, the invention provides a recombinant protein comprising a physical analog polypeptide of a reference protein sequence wherein the analog polypeptide: (i) has the same amino acid composition as the reference protein sequence; and (ii) has a primary sequence that has less than 50% identity, e.g., less than 40% identity, less than 30% identity, or less than 20% identity, to the reference protein sequence across the length of the reference sequence. In some embodiments, the reference sequence is at least 50, at least 60, at least 70, at least 80, at least 90, or at least 100 amino acids in length. In some embodiments, the engineered protein sequence has at least 50% identity, or at least 60%, at least 70%, at least 80% identity, at least 85% identity, at least 90% identity, or at least 95%, or greater, identity to the amino acid sequence set forth in SEQ ID NO:2, SEQ ID NO:4, SEQ ID NO:6, or SEQ ID NO:8. In some embodiments, the analog polypeptide comprises a reverse sequence of at least 25 amino acids in length where the sequence is reversed in comparison to the reference protein sequence, e.g., a reference sequence set forth in SEQ ID NO:1, SEQ ID NO:3, SEQ ID NO:5, or SEQ ID NO:7. In some embodiments, the analog polypeptide comprises a scrambled subsequence (determined with reference to the corresponding subsequence of the reference sequence) of at least 25 amino acids in length e.g., a reference sequence set forth in SEQ ID NO:1, SEQ ID NO:3, SEQ ID NO:5, or SEQ ID NO:7. In some embodiments, the protein comprises at least two repeated analog polypeptide sequences. In some embodiments, the protein comprises at least four repeated analog polypeptide sequences. In some embodiments, the recombinant protein comprises the sequence set forth in SEQ ID NO:2, SEQ ID NO:4, SEQ ID NO:6, or SEQ ID NO:8.

In another embodiment, the invention provides a molecular weight marker composition comprising an aqueous solution and an engineered protein comprising a physical analog polypeptide of the invention as described herein. In some embodiments, the molecular weight marker composition comprises a physical analog polypeptide, wherein the analog polypeptide: (i) has the same amino acid composition as a reference protein sequence; and (ii) has a primary sequence that has less than 50% identity to the reference protein sequence. In some embodiments, the amino acid sequence of the recombinant protein present in the molecular weight marker composition has at least 50% identity, or at least 60%, at least 70%, at least 80% identity, at least 85% identity, at least 90% identity, or at least 95%, at least 96%, at least 97%, at least 98%, or at least 99%, or greater, identity to the amino acid sequence set forth in SEQ ID NO:2, SEQ ID NO:4, SEQ ID NO:6, or SEQ ID NO:8; or has the amino acid sequence set forth in SEQ ID NO:2, SEQ ID NO:4, SEQ ID NO:6, or SEQ ID NO:8. In some embodiments, the amino acid sequence of the recombinant protein present in the molecular weight marker composition has a subsequence of at least 25 amino acids in length where the sequence is reversed as determined with reference to a reference protein sequence, e.g., a reference sequence set forth in SEQ ID NO:1, SEQ ID NO:3, SEQ ID NO:5, or SEQ ID NO:7. In some embodiments, molecular weight marker composition comprises a physical analog polypeptide that comprises a scrambled subsequence (determined with reference to the corresponding subsequence of the reference sequence) of at least 25 amino acids in length e, e.g., a reference sequence set forth in SEQ ID NO:1, SEQ ID NO:3, SEQ ID NO:5, or SEQ ID NO:7. In some embodiments, the engineered protein present in the molecular weight marker composition comprises at least two repeated analog polypeptide sequences. In some embodiments, the protein comprises at least four repeated analog polypeptide sequences. In some embodiments, the recombinant protein present in the molecular weight marker composition comprises the sequence set forth in SEQ ID NO:2, SEQ ID NO:4, SEQ ID NO:6, or SEQ ID NO:8.

In some embodiments, a molecular weight marker composition of the invention comprises at least two engineered polypeptides, or at least three, at least four, or at least 5 engineered polypeptides as described herein. In some embodiments, the molecular weight marker composition that comprises at least one engineered protein comprising a physical analog peptide of the invention provides a molecular weight marker range, e.g., from about 2.5 kDa or 3 kDa to about 250 kDa in size.

In another aspect, the invention provides a kit comprising a molecular weight marker composition comprising at least one engineered protein of the invention.

In further aspects, the invention provides a method of determining the size of a protein of interest present in a sample, the method comprising electrophoresing a sample comprising the protein of interest under denaturing conditions; co-electrophoresing a molecular weight marker composition of the invention as described herein; and comparing the size of the protein in the sample to the molecular weight markers present in the molecular weight marker composition, thereby determining the size of the protein present in the sample.

In another aspect, the invention provides a method of preparing a molecular weight marker composition, the method comprising: expressing an engineered protein of the invention as described herein in a bacterial host cell; and purifying the protein. In some embodiments, the method further comprises admixing the engineered protein with another protein molecular weight marker. In some embodiments, the engineered protein (i) has the same amino acid composition as the reference protein sequence; and (ii) has a primary sequence that has less than 50% identity, e.g., less than 40% identity, less than 30% identity, or less than 20% identity, to the reference protein sequence across the length of the reference sequence. In some embodiments, the analog polypeptide comprises a reverse sequence of at least 25 amino acids in length where the sequence is reversed in comparison to the reference protein sequence, e.g., a reference sequence set forth in SEQ ID NO:1, SEQ ID NO:3, SEQ ID NO:5, or SEQ ID NO:7. In some embodiments, the analog polypeptide comprises a scrambled subsequence (determined with reference to the corresponding subsequence of the reference sequence) of at least 25 amino acids in length e, e.g., a reference sequence set forth in SEQ ID NO:1, SEQ ID NO:3, SEQ ID NO:5, or SEQ ID NO:7. In some embodiments, the method comprises admixing at least one recombinant protein selected from the group consisting of SEQ ID NO:2, SEQ ID NO:4, SEQ ID NO:6, or SEQ ID NO:8 with another protein. In some embodiments, the method further comprises admixing at least one recombinant protein selected from the group consisting of SEQ ID NO:2, SEQ ID NO:4, SEQ ID NO:6, or SEQ ID NO:8 with marker proteins of different sizes to provide a range of molecular weight marker proteins having molecule weights about 2.5 kDa or 3 kDa to about 250 kDa. In some embodiments, the method comprises admixing a recombinant protein the has a sequence that has at least 50% identity, or at least 60%, at least 65%, at least 70%, at least 75%, at least 80%, at least 85%, at least 90%, or at least 95%, or greater, amino acid sequence identity to SEQ ID NO:2, SEQ ID NO:4, SEQ ID NO:6, or SEQ ID NO:8 with another protein to provide marker proteins of different sizes, e.g., to provide molecular weight marker proteins having a desired range, e.g., from about 2.5 kDa or 3 kDa to about 250 kDa.

In further aspects, the invention provides a recombinant protein comprising a physical analog polypeptide reference protein sequence, wherein the analog polypeptide: (i) has the same amino acid composition as a reference protein sequence, e.g., a reference protein sequence set forth in SEQ ID NO:1, SEQ ID NO:3, SEQ ID NO:5, or SEQ ID NO:7; and (ii) has a primary sequence that has less than 50% identity to the reference protein sequence, wherein the reference protein is 100 amino acids or more in length.

BRIEF DESCRIPTION OF THE DRAWINGS

FIG. 1 provides an example of sequence alignments of three reference proteins (SEQ ID NOS:3, 5 and 7) and their counterpart reversed protein sequences (SEQ ID NOS:4, 6 and 8).

DETAILED DESCRIPTION OF THE INVENTION

Definitions

Figure 2:
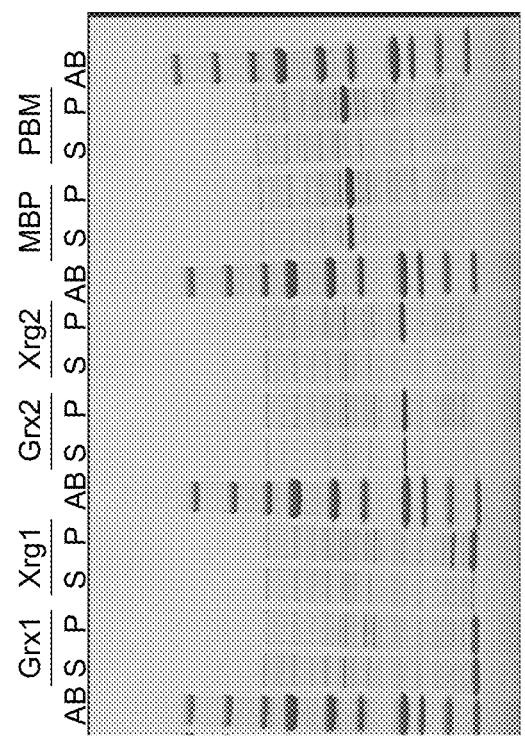
FIG. 2 provides data showing the solubility of overexpressed proteins with their reversed counterparts. Cell pastes over-expressing the reversed proteins with their corresponding original version were lysed in IMAC native lysis buffer by sonication. The supernatants (S) or pellets (P) after centrifugation from each cell paste was separated on SDS-PAGE. All Blue Protein Standards (AB) was used as the migration marker. U, uninduced; I, induced.

The term "physical analog polypeptide" as used herein refers to a non-naturally occurring protein analog that has the same amino acid composition (i.e., has the same amino acid content over the length of the sequence) of a reference polypeptide of interest, but has a primary sequence that has less than 65% identity, typically less than 60%, 50%, 45%, 40%, 35%, 30% or 25% identity or less, to the primary sequence of the reference protein. Thus, a "physical analog polypeptide" has the same physical properties (e.g., the same isoelectric point, the same extinction coefficient, the same number of lysines or primary amine groups for labeling) as the denatured reference protein, but has a different sequence. The physical analog polypeptide is of the same amino acid composition and thus is the same length as the reference protein. However, the physical analog polypeptide may be contained in a longer protein.

A "reference protein" as used herein refers to a protein sequence of interest to which the physical analog is compared. In some embodiments, a "reference protein" sequence of interest for this invention is at least 25, 30, 35, 40, 45, 50, 60, 70, 80, 90, or 100, or more, amino acids in length.

As used herein, a "reverse sequence" refers to a protein sequence of at least 15 amino acids, often at least 20, 25, 30, or 50 or more amino acids in length, that relative to a reference protein of interest, is the sequence of the reference protein when read in the C-terminal to the N-terminal direction.

The term "scrambled sequence" or "shuffled sequence" as used herein refers to a sequence of a polypeptide that is different in comparison to a reference sequence, but is of the same length and amino acid compositions. The "scrambled sequence" may contain the same amino acids of the reference sequence in any order, so long as it does not match the reference sequence across the region of interest.

A "scrambled sequence" or "reverse sequence" is determined with reference to a protein sequence of interest, e.g., SEQ ID NO:1, SEQ ID NO:3, SEQ ID NO:5, or SEQ ID NO:7, or a reference sequence that is substantially identical to SEQ ID NO:1, SEQ ID NO:3, SEQ ID NO:5, or SEQ ID NO:7, when the sequences are aligned across their length.

An "engineered protein" in the context of this invention refers to a protein that contains one or more physical analog polypeptide sequences.

A "molecular weight marker mixture" in the context of this invention refers to a composition comprising multiple polypeptides having different molecular weights such that the polypeptides serve as a comparison standard for evaluating the size of one or more polypeptides of interest. In some embodiments of the invention, a molecular weight marker mixture comprises at least two polypeptides that have a common sequence, e.g., of at least 50 amino acids or more, where the common sequence is repeated a different number of times in the polypeptides. For example, in one polypeptide that is a member of the molecular weight marker mixture, the common sequence may be present one time, in a second polypeptide member of the ladder, the sequence may be repeated, so that it is present two times, or three times, or four times, or more.

The terms "nucleic acid" and "polynucleotide" are used synonymously and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones. Thus, nucleic acids or polynucleotides may also include modified nucleotides, that permit correct read through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine, hypoxanthine, isocytosine, isoguanine, etc.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer. In some embodiments, an engineered protein of the invention may comprises one or more non-naturally occurring amino acids, but the physical analog polypeptide component of the engineered protein retains the physical characteristics, e.g., amino acid composition, size, etc. of the denatured reference protein.

"Percentage of sequence identity" is determined by comparing two optimally aligned sequences over a comparison window. In the current invention, the reference protein sequence and physical analog polypeptide have the same amino acid composition, accordingly the sequences that are compared are often of the same length and do not comprise gaps. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. A "comparison window", as used herein, includes reference to a segment of any one of the number of contiguous positions, e.g., 20 to 600, usually about 50 to about 200, more usually about 100 to about 150, or over the entire length of the reference protein sequence and physical analog sequence being compared. Alignment of sequences for comparison may be conducted using many known programs, e.g., by the local homology algorithm of Smith and Waterman Adv. Apl. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85: 2444 (1988), by computerized implementations of these algorithms (e.g., BLAST, FASTA), or by inspection.

A protein sequence that is "substantially identical" to a reference protein sequence, has at least 60% identity, at least 70% identity, at least 75% identity, at least 80% identity, at least 85% identity, at least 90% identity, or at least 95% identity or greater to a reference protein sequence across the length of the reference sequence. When referring to percent identity to a protein containing other sequences that are not from the reference protein sequence of interest, such as a purification tag, e.g., His or Strep I tag, the percent identity is determined relative to the amino acid sequence that excludes sequences, such as a His or Strep I tag.

Introduction

The invention is based, in part on the discovery that amino acid sequences of native proteins, e.g., reference proteins, can be arranged with one or more of the following strategies: 1) reversed entirely from C-terminus to N-terminus or reversed entirely from C-terminus to N-terminus except for the first few (e.g., the first 1, 2, 3, 4, 5, 6, 7, 8, 9, or 10 amino acids) and/or the last few, (e.g., the last 1, 2, 3, 4, 5, 6, 7, 8, 9, or 10 amino acids); 2) reversal of one or more individual small domains within the reference protein and/or, 3) randomly shuffled and recombined. Such strategies provide engineered proteins that retain physical/chemical characteristics of native proteins, for example, retain the same isoelectric point, same amino acid composition, same extinction coefficient, similar migration on different types of polyacrylamide gel electrophoresis, similar chromatography characteristics, similar dye labeling pattern due to the same number of reactive primary amine groups that are in similar micro-environments, and/or similar SDS-binding pattern. The engineered proteins of the invention, however, have different primary sequences, and likely different secondary and tertiary structures from the native proteins.

Physical Analog Polypeptides

This invention employs routine techniques in the field of recombinant genetics relating to synthesizing polynucleotides encoding a polypeptide of interest and expressing those polynucleotides in an expression system. Generally, the nomenclature and the laboratory procedures in recombinant DNA technology described below are those well known and commonly employed in the art. Basic texts disclosing the general methods of use in this invention include Sambrook & Russell, Molecular Cloning, A Laboratory Manual (3rd Ed, 2001); Kriegler, Gene Transfer and Expression: A Laboratory Manual (1990); and Current Protocols in Molecular Biology (Ausubel et al., eds., 1994-2009, Wiley Interscience).

For proteins, sizes are given in kilodaltons (kDa) or amino acid residue numbers.

Oligonucleotides can be obtained from any number of vendors, or chemically synthesized.

In some embodiments, e.g., proteins of 50 amino acids or greater in length, the protein is expressed using recombinant expression technology. In some embodiments, e.g., small proteins, such as a protein that is smaller than 50 amino acids, the protein may be chemically synthesized.

Physical Analog Polypeptide Design

Physical analog polypeptides have the same amino acid composition as a polypeptide of interest, but differ in primary sequence. A physical analog polypeptide can therefore be obtained by reversing a polypeptide sequence of interest, or reversing a region within the polypeptide sequence of interest. A physical analog polypeptide can also be obtained by scrambling or shuffling sequences within the polypeptide sequence of interest. Combinations of reversing and scrambling/shuffling may also be used to obtain a physical analog polypeptide. A physical analog polypeptide of the invention can be of various sizes, for example, the physical analog polypeptide may have a molecular weight of 10 kDa, 25 kDa, or 50 kDa. In some embodiments, the physical analog peptide is at least 15, at least 20, at least 25, at least 50, at least 75, at least 100, at least 200, or at least 300 amino acids in length. In some embodiments the length of the reversed sequence, relative to the reference sequence, present in a physical analog peptides is at least 15, at least 20, at least 25, at least 50, at least 60, at least 70, at least 80, at least 90, at least 100, at least 200, or at least 300 amino acids.

A physical analog polypeptide of this invention need not have all of the sequences reversed or scrambled when comparing the analog polypeptide sequence to the reference polypeptide sequence of interest. The analog polypeptide need only be sufficiently reversed and/or scrambled so that the analog polypeptide primary sequence has less than 60% identity, e.g., less than 55% identity, or less than 50% identity, to the reference polypeptide sequence of interest. In some embodiments, the physical analog protein has less than 45%, less than 40%, less than 30%, or less than 20% amino acid sequence identity to the reference polypeptide sequence of interest.

In some embodiments, a physical analog polypeptide is constructed by reversing at least 50%, 60%, 70%, 80%, or 90%, or greater of the reference polypeptide sequence of interest. Thus, in some embodiments, a subsequence within the reference polypeptide sequence of interest may be reversed. Such a subsequence may be, e.g., at least 10, 15, 20, 25, 30, 35, 40, 45, 50, 55, 60, 65, 70, 75, 80, 85, 90, 95, 100, or 105 contiguous amino acids, or greater, in length. Reversed polypeptides may then be obtained, e.g., by synthesizing nucleic acids that encode the sequences and expressing the polypeptides in an expression system.

Similarly, a physical analog polypeptide can be constructed by scrambling or shuffling at least 50%, 60%, 70%, 80%, or 90%, or greater of the reference polypeptide sequence of interest. Thus, in some embodiments, a subsequence within the reference polypeptide sequence of interest may be scrambled or shuffled when compared to the primary sequence of the reference polypeptide sequence. Such a subsequence may be, e.g., at least 10, 15, 20, 25, 30, 35, 40, 45, 50, 55, 60, 65, 70, 75, 80, 85, 90, 95, 100, or 105 contiguous amino acids, or greater, in length. In some embodiments, a sequence can be shuffled or randomized using a computer program (e.g., Stothard, *Biotechniques* 28:1102-1104, 2000, see also the Sequence Manipulation Suite at biowww.net (biowww.net/sms2/shuffle_protein.html). Shuffled polypeptides may then be obtained by synthesizing nucleic acids that encode the sequences.

In some embodiments, a combination of reversing sequence and scrambling sequences can be employed to obtain a physical analog polypeptide of interest. Thus, for example, part of the sequence of the analog polypeptide may be reversed when compared to the reference sequence whereas part of the sequence may be scrambled in comparison to the reference sequence.

The physical analog polypeptide may be part of a longer protein that comprises tags or other protein elements, including additional copies of the physical analog polypeptide that are linked together to form a longer polypeptide. For example, a reverse peptide may be contained in a longer engineered protein that comprises multiple copies of the reverse peptide.

One of ordinary skill in the art further understands that it may be beneficial to retain some of the amino acid residues in the normal order in which they occur in the reference protein sequence. For example, it may be desirable to retain the N-terminal amino acid residues of the reference polypeptide sequence of interest, e.g., a starting methionine, or an amino acid that may undergo processing. Thus, in some embodiments, at least 1, 2, 3, 4, 5, 6, 7, 8, 9, or 10 N-terminal amino acid residues from the reference protein may be retained at the N-terminus of the physical analog polypeptide.

In some embodiments, a physical analog peptide of the invention is an analog based on a reference sequence set forth in SEQ ID NO:1, SEQ ID NO:3, SEQ ID NO:5, or SEQ ID NO:7. In some embodiments, all of the amino acids, or a subsequence of at least 29, 28, 27, 26, 25, 20, or 15 amino acids, of SEQ ID NO:1 are reversed and/or scrambled to make a physical analog polypeptide of the invention. In some embodiments, all of the amino acids, or a subsequence of at least 84, 80, 70, 60, 50, or 40 amino acids, of SEQ ID NO:3 are reversed and/or scrambled to make a physical analog polypeptide of the invention. In some embodiments, all of the amino acids, or a subsequence of at least 214, 210, 200, 180, 160, 140, 120, 110, or 100 amino acids, of SEQ ID NO:5 are reversed and/or scrambled to make a physical analog polypeptide of the invention. In some embodiments, all of the amino acids, or a subsequence of at least 220, 210, 200, 180, 160, 140, 120, 110, or 100 amino acids, of SEQ ID NO:7 are reversed and/or scrambled to make a physical analog polypeptide of the invention.

In some embodiments, a physical analog peptide sequence, e.g., SEQ ID NO:2 or SEQ ID NO:4 (without the His tag), may be repeated in a recombinant protein sequence to provide proteins of increasing size. The physical analog polypeptide sequences within such a protein may be separated by linkers, or may be joined directly. Further, the ends of the proteins may be additionally modified to provide sequences to facilitate manipulation of the protein. For example, in some embodiments, a recombinant polypeptide comprising a physical analog polypeptide may contain tag sequences, e.g., poly-His, FLAG, or other sequences, to assist in purification of the protein.

In some embodiments, the invention provides variants of physical analog peptides, e.g., variants of SEQ ID NO:2, SEQ ID NO:4, SEQ ID NO:6, or SEQ ID NO:8. Such variants can be used, e.g., as molecular weight markers. In some embodiments, a variant has at least 75% identity, typically at least 80% identity, more typically at least 85%, 90%, 95%, 96%, 97%, 98%, 99%, or greater identity to SEQ ID NO:2, SEQ ID NO:4, SEQ ID NO:6, or SEQ ID NO:8. In some embodiments, the variants retain at least the first five N-terminal amino acids of SEQ ID NO:2, SEQ ID NO:4, SEQ ID NO:6, or SEQ ID NO:8. Variants may be generated that include conservative substitutions that are designed to maintain the overall charge of physical analog peptide. In typical embodiments, substitutions are employed that maintain the size of the physical analog polypeptide.

Spacers (also referred to herein as linkers) are well known in the art. Typical peptide linker sequences contain Gly, Ser, Ala and Thr residues. Useful linkers include glycine-serine polymers (including, for example, (GGGGS)n (SEQ ID NO:10), (GS)n, (GSGGS)n (SEQ ID NO:11), and (GGGS)n (SEQ ID NO:12), where n is an integer of at least one); glycine-alanine polymers; alanine-serine polymers; and other flexible linkers.

Synthesis and Expression of Physical Analog Polypeptides

In some embodiments, a physical analog polypeptide of the invention may be synthesized chemically using known peptide synthesis techniques. In preferred embodiments, a physical analog polypeptide is obtained by expressing recombinant nucleic acid sequences that encode the physical analog polypeptide.

In typical embodiments, synthetic oligonucleotides can be used to construct genes encoding a physical analog polypeptide for expression of the protein. This method is performed using a series of oligonucleotides, e.g., 40-120 bp in length that have overlapping ends. Typically, the method is employed in combination with PCR to assemble the overlapping fragments to obtain a full-length nucleic acid that encodes a physical analog polypeptide of the invention.

In some embodiments, regions of the reference protein that have sequences that are not reversed or shuffled may be obtained using techniques such as PCR (where a nucleic acid sequence encoding the reference protein is already available). Such a region can then be combined with polynucleotides encoding the reversed or shuffled sequences.

To obtain high level expression of a cloned gene, such as nucleic acid sequences encoding SEQ ID NO:4, SEQ ID NO:6, or SEQ ID NO:8, a nucleic acid sequence encoding the polypeptide is subcloned into an expression vector that contains a promoter to direct transcription, a transcription/translation terminator, and additional sequences, such as a ribosome binding site for translational initiation. The promoter is operably linked to the nucleic acid sequence encoding the polypeptide of the invention. In typical embodiments, a bacterial expression system is employed to obtain high expression levels. Expression vectors useful in the present invention include chromosomal-, episomal- and virus-derived vectors, e.g., vectors derived from bacterial plasmids or bacteriophages, and vectors derived from combinations thereof, such as cosmids and phagemids.

The elements that are typically included in expression vectors also include a replicon that functions in $E.$ $coli$, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable.

Suitable bacterial promoters are well known in the art and described, e.g., in Sambrook et al. and Ausubel et al. Appropriate promoters, include the bacteriophage lambda $P_L$ promoter, the bacteriophage T7 promoter, the $E.$ $coli$ lac, tip and tac promoters, and the like. Other suitable promoters will be known to the skilled artisan. The gene fusion constructs also contain additional sequences for expression, e.g., transcription initiation and termination sites.

Vectors suitable for use in the invention are well known and are commercially available and include vectors such as Phagescript vectors, Bluescript vectors, pET vectors, pGEX vectors and others, pTrx vectors, pTrc vectors, pFLAG vectors, etc. Other suitable vectors are also available. Bacterial expression systems for expressing the polypeptides are also available for bacteria such as *Bacillus* sp., and *Salmonella*. Kits for such expression systems are commercially available. Eukaryotic expression systems may also be employed to express the polypeptides of the invention. Such expression systems, e.g., expression systems that function in mammalian cells, yeast, or insect cells, are well known in the art and are also commercially available.

Standard transfection methods are used to produce cell lines that express large quantities of polypeptides of the invention, which are then purified using standard techniques. For example, any of the well known procedures for introducing foreign nucleotide sequences into host cells may be used. These include the use of calcium phosphate transfection, DEAE dextran-mediated transfection, polybrene, electroporation, liposomes, or any of the other well known methods for introducing cloned genomic DNA, cDNA, synthetic DNA or other foreign genetic material into a host cell (see, e.g., Sambrook et al., supra; and Ausubel, supra). It is only necessary that the particular genetic engineering procedure used be capable of successfully introducing at least one gene into the host cell capable of expressing a polypeptide of the invention.

After the expression vector is introduced into the cells, the transfected cells are cultured under conditions favoring expression of a polypeptide of the invention. Polypeptides of the invention are recovered from the culture using standard techniques, such as those employed in the examples provided in the EXAMPLES section.

In some embodiments, e.g., where it may be desirable to obtain a molecular weight marker ladder that contains multiple proteins, including at least one protein engineered in accordance with the invention, proteins may be expressed on a single expression vector or using multiple expression vectors. For example, individual nucleic acids that encode each protein to be included in the molecular weight marker set may be expressed in one or more expression vectors. Thus, in some embodiments, the proteins to be used in the marker set may be expressed using a separate expression vector for each protein. In some embodiments, more than one protein may be encoded in a single vector. In some embodiments, multiple proteins may be encoded in a single vector where expression is driven by multiple promoters. In some embodiments, the multiple proteins may be produced where expression is driven by a single promoter. In some embodiments, the proteins that make up a desired set of marker proteins may be expressed from the vector as a single protein, which is then cleaved at suitable sites to produce the desired protein sizes.

Host cells may be transformed with a nucleic acid encoding multiple proteins, or may be transformed with multiple expression vectors encoding different protein.

Proteins can then be purified using known techniques, e.g., purification tags, and the proteins may be mixed to provide molecular weight standards that have the desired range of sizes.

Molecular Weight Markers

The invention also provides molecular weight markers that comprise one or more physical analog polypeptides of the invention. Thus, a physical analog polypeptide as described herein may be used to prepare a set of molecular weight markers, e.g., a protein molecular weight ladder, that can be used as sizing standards in protein analysis techniques such as electrophoresis. In some embodiments a molecular weight ladder may be obtained by making a series of proteins that have different numbers of repeats of a physical analog polypeptide, e.g., SEQ ID NO:2 and SEQ ID NO:4. For example, a nucleic acid sequence encoding SEQ ID NO:2 may be repeated in an expression vector to obtain protein molecular weight markers of a higher molecular weight.

The molecular weight increments of a molecular weight ladder may be provided by changing the length of the gene encoding the components of the ladder, e.g., by changing the number of copies of a physical analog polypeptide. Thus, a molecular weight ladder can range in size, e.g., from about 2 kDa or 3 kDa to about to about 300 kDa, from about 3 kDa to about 250 kDa, often from about 10 kDa to about 250 kDa in increments of, for example, 2 kDa, 3 kDa, 5 kDa, 10 kDa, 20 kDa, 25 kDa, 50 kDa, 100 kDa, 200 kDa or greater.

The molecular weight markers that comprise at least one engineered protein comprising a physical analog polypeptide of the invention may be unstained prior to use, e.g., in polyacrylamide gel electrophoresis, or may be prestained with one or more protein-binding dyes. Many protein-binding dyes are known in the art. For example, any dye that binds covalently to one or more of the marker proteins may be used, including visible dyes (chromophores), fluorescent dyes (fluorophores), phosphorescent dyes (phosphors) and the like. In some embodiments the dye may be remazol brilliant blue R (RBBR), eosin isothiocyanate, malachite green isothiocyanate, reactive orange (also known as procion yellow), procion red, fluorescein isothiocyanate, rhodamine isothiocyanate, eosin iodoacetamide, reactive black 5, Remasol brilliant violet 5R, reactive orange 14, and the like. Such dyes are available commercially, for example from Sigma/Aldrich (St. Louis, Mo.) and Life Technologies. Additional dyes are described, e.g., in U.S. Pat. No. 6,995,023.

In some embodiments, molecular weight markers that comprise at least one engineered protein of the invention that comprises a physical analog polypeptide can be used for western blotting applications. For example, one or more physical analog polypeptides, such as those set forth in SEQ ID NO:2, SEQ ID NO:4, SEQ ID NO:6, or SEQ ID NO:8, may be present in a set of molecular weight markers that is separated on a gel under denaturing conditions with one or more samples that comprise a protein(s) of interest. Following transfer of the separated proteins to a membrane, the membrane is incubated with an antibody to the protein of interest. The molecular weight markers of the invention typically do not bind to antibodies, as the markers have sequences that are unrelated to known proteins.

Molecular weight marker solutions comprising proteins of the invention may include additional components such as buffering agents, detergents, and the like.

Kits

The invention also provides kits comprising the engineered proteins of the invention, e.g., a kit comprising molecular weight marker proteins. Such proteins may be unstained or pre-stained. The kit can comprise individual containers, e.g., a tube or vial, containing the recombinant proteins of the invention, or may include containers with more than one recombinant protein of the invention. In some embodiments, a kit may contain additional reagents, e.g., buffers, solutions, for the application for which the kit is intended, e.g., denaturing polyacrylamide gel electrophoresis. Thus, in some embodiments, a kit may comprise a container holding a solution that comprises molecular weight markers that have at least one engineered protein of the invention. In some embodiments, such a solution may comprise two, three, or four engineered proteins of the invention.

EXAMPLES

Example 1

Comparison of Physical Analog Polypeptides to Reference Proteins

Figure 1:
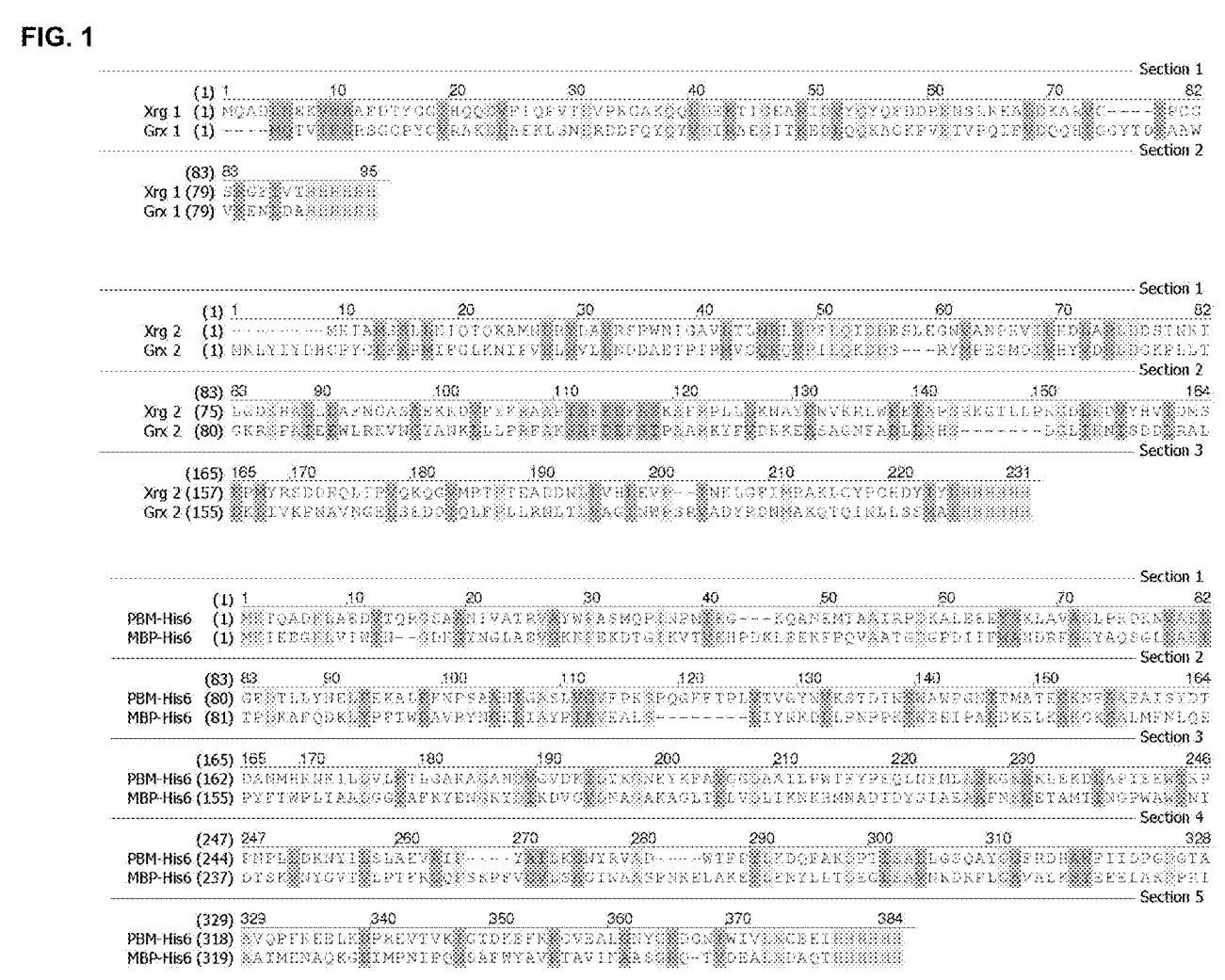

Physical analog peptide based on reversed sequences of the reference sequences BinB, Grx1, Grx2, and MBP were created. Examples of alignments of the reference sequences and reversed counterparts for three references sequences are shown in FIG. 1. There is very little sequence identity between the reference sequence when aligned with its reversed counterpart.

The solubility of the reference proteins in comparison to their reversed counterparts was analyzed (FIG. 2). Nucleic acids encoding the reference proteins and the reversed proteins were individually subcloned into the pET28 expression vector to obtain the recombinant plasmids. The plasmids were transformed into BL21 (DE3) cells for expression. Cell pastes from cells that over-expressed the reversed analog proteins and the reference proteins were lysed in IMAC native elution buffer by sonication. The supernatants (S) or pellets (P) after centrifugation from each cell paste were separated on SDS-PAGE. The results showed that the analog proteins were largely insoluble in comparison to the reference proteins.

Figure 3:
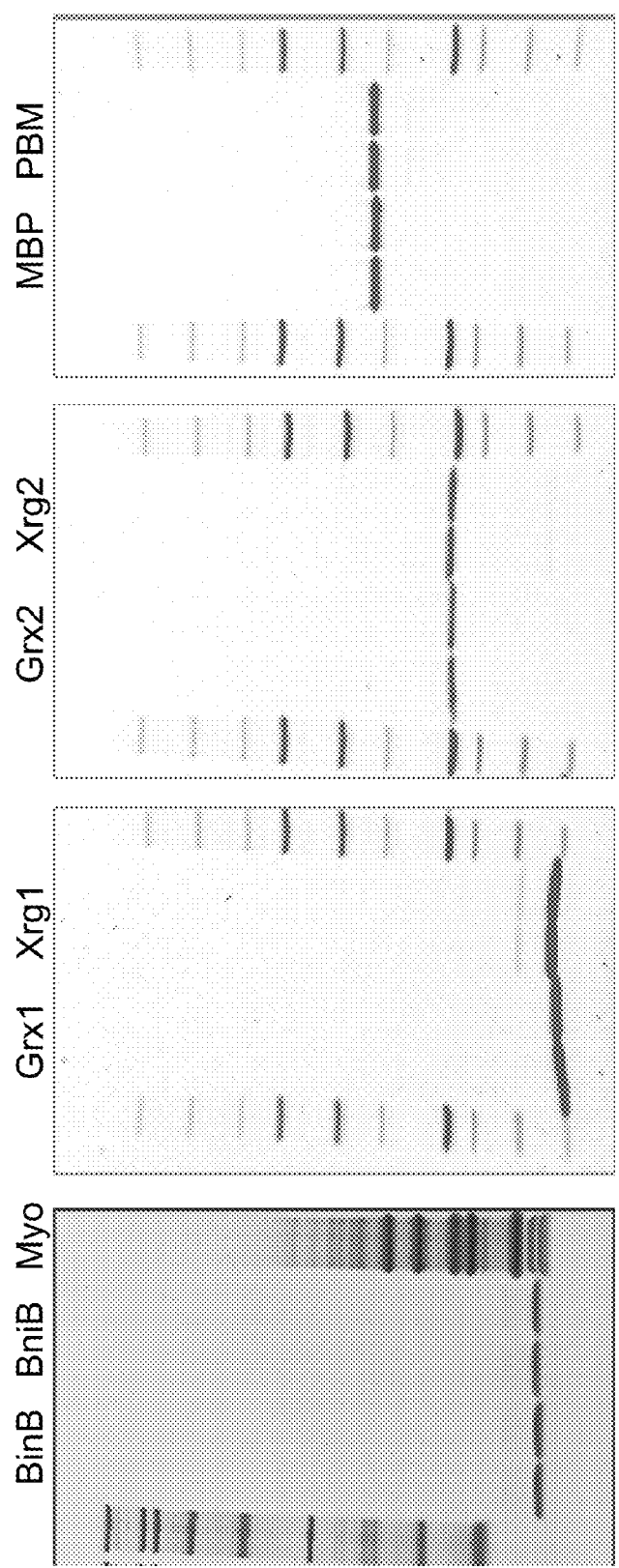
FIG. 3 shows migration of synthesized peptides and purified proteins with reversed counterparts. The same amount of synthesized peptides and denaturing IMAC purified proteins with their reversed counterparts in duplicate were separated on 10-20% Criterion Tris-Tricine (left) or 4-20% Criterion Tris-HCl (right 3 gels) gels and imaged by GS-800 densitometer. Precision Plus Unstained Protein Standards or Myoglobin standards were used as the migration marker.

FIG. 3 shows migration of the synthesized peptides and purified proteins with reversed counterparts on a polyacrylamide gel.

Figure 4:
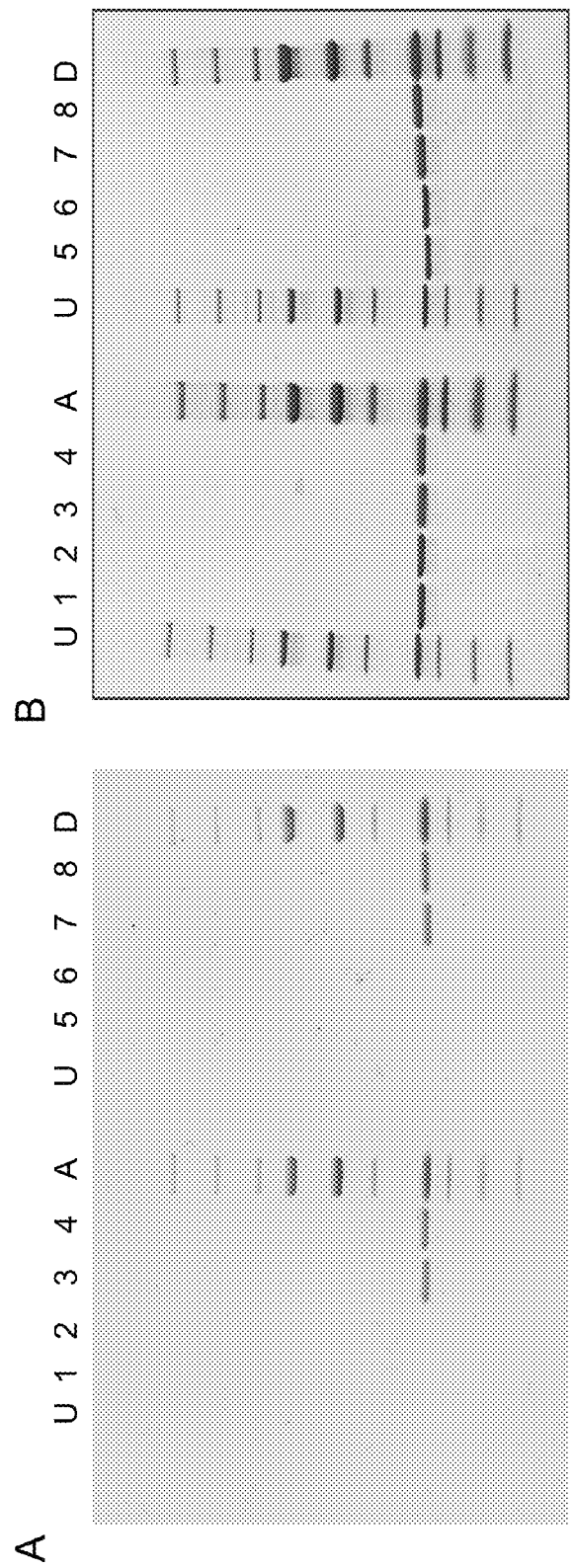
FIG. 4 shows the migration performance of the an illustrative physical analog protein (reverse protein 1) with or without covalent dye-labeling. A, the gel picture before Bio-Safe staining B, the gel picture after Bio-Safe staining U, Unstained Precision Plus protein stds; A, All Blue Precision Plus protein stds; D, Dual Color Precision Plus protein stds; 1, reverse protein; 2, reference protein; 3, Uniblue-reversed protein; 4, Uniblue-reference protein; 5, reverse protein; 6, reference protein; 7, TRITC-reverse protein; 8, TRITC-reference protein.

FIG. 4 shows the migration performance of an illustrative reversed protein (reverse protein 1) with or without covalent dye-labeling in comparison to the reference protein.

Figure 5:
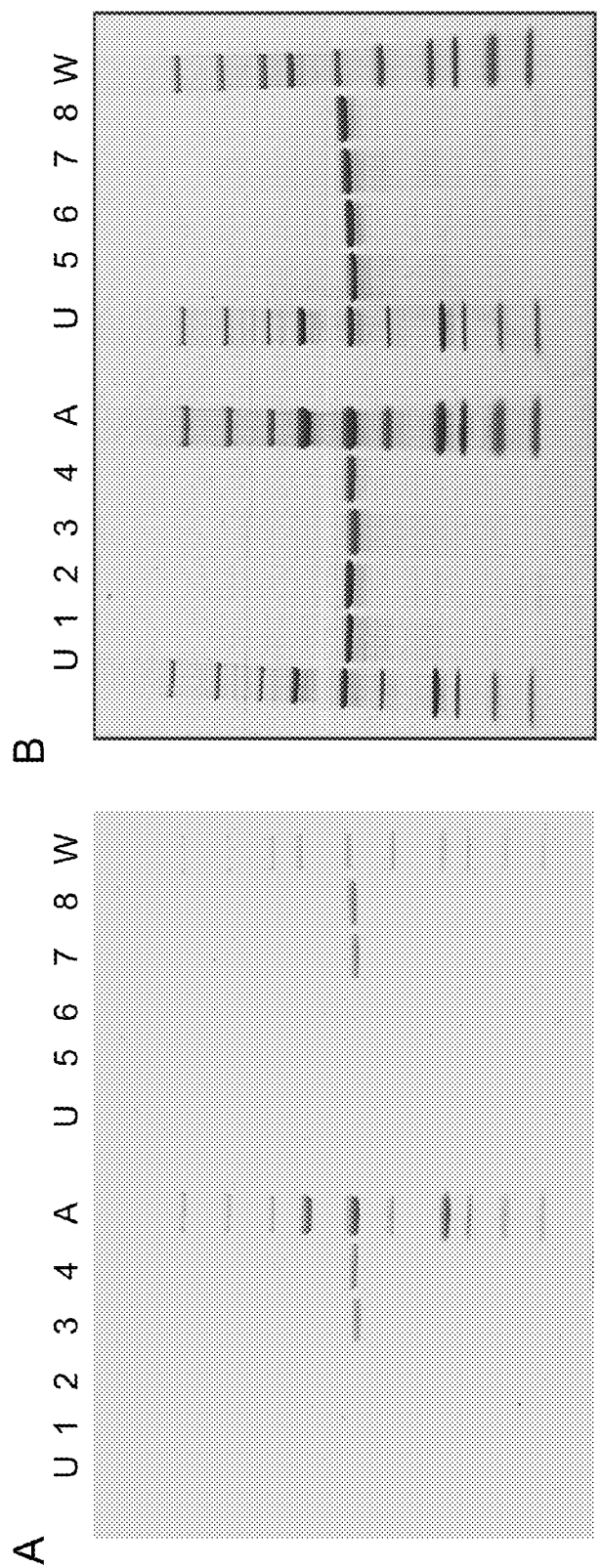
FIG. 5 shows the migration performance of a second illustrative physical analog protein (reverse protein 2) with or without covalent dye-labeling. A, the gel picture before Bio-Safe staining; B, the gel picture after Bio-Safe staining; U, Unstained Precision Plus protein stds; A, All Blue Precision Plus protein stds; W, WesternC Precision Plus protein stds; 1, reverse protein; 2, reference protein; 3, Uniblue-reverse protein; 4, Uniblue-reference protein; 5, reverse protein; 6, reference protein; 7, TRITC-reverse protein; 8, TRITC-reference protein.

FIG. 5 shows the migration performance of a second illustrative reversed protein (reverse protein 2) with or without covalent dye-labeling in comparison to the reference protein.

Figure 6:
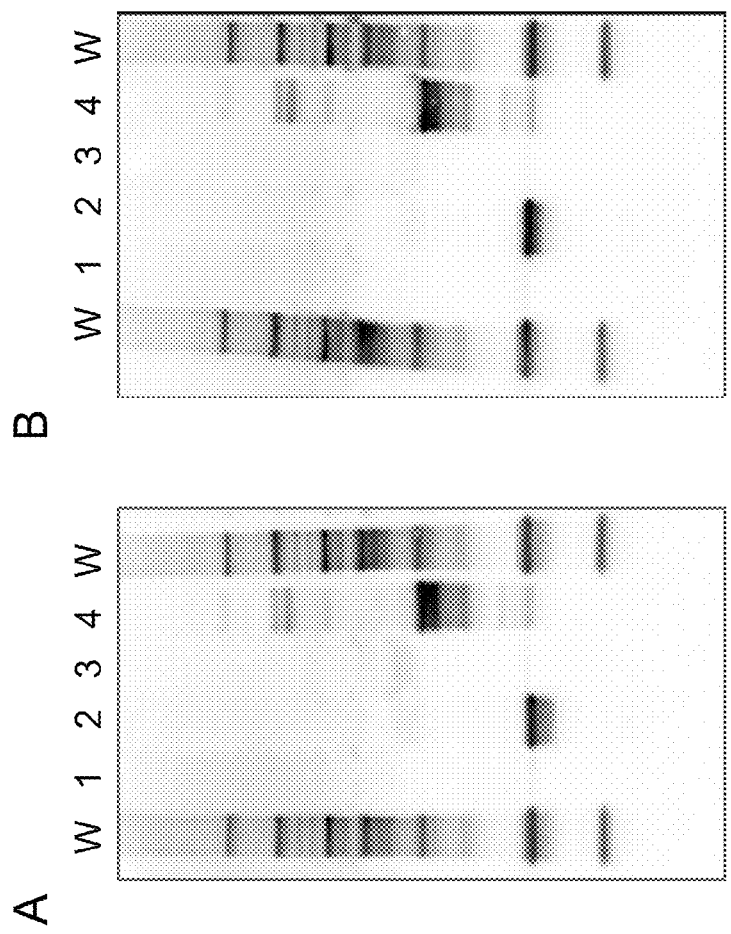
FIG. 6 shows a western blot analysis of reverse proteins. A, 0.2 µg of reverse protein (1 and 3 for reverse protein 1 and reverse protein 2, respectively) and reference protein (2 and 4 for reference protein 1 and reference protein 2, respectively). Proteins were separated on a 4-20% Tris-HCl gel and transferred onto PVDF membrane. Primary polyclonal antibodies to reference protein 1 were used with HRP-conjugated Goat-anti-Rabbit secondary antibody. The blot was developed using an Immuno-Star WesternC Chemiluminescent kit and imaged on the ChemiDoc XRS. 5 µl Precision Plus WesternC standards was included as control.

FIG. 6 shows a western blot analysis of a reversed protein in comparison to the reference protein.

Example 2

Use of Physical Analog Proteins for Protein Standards

Figure 7:
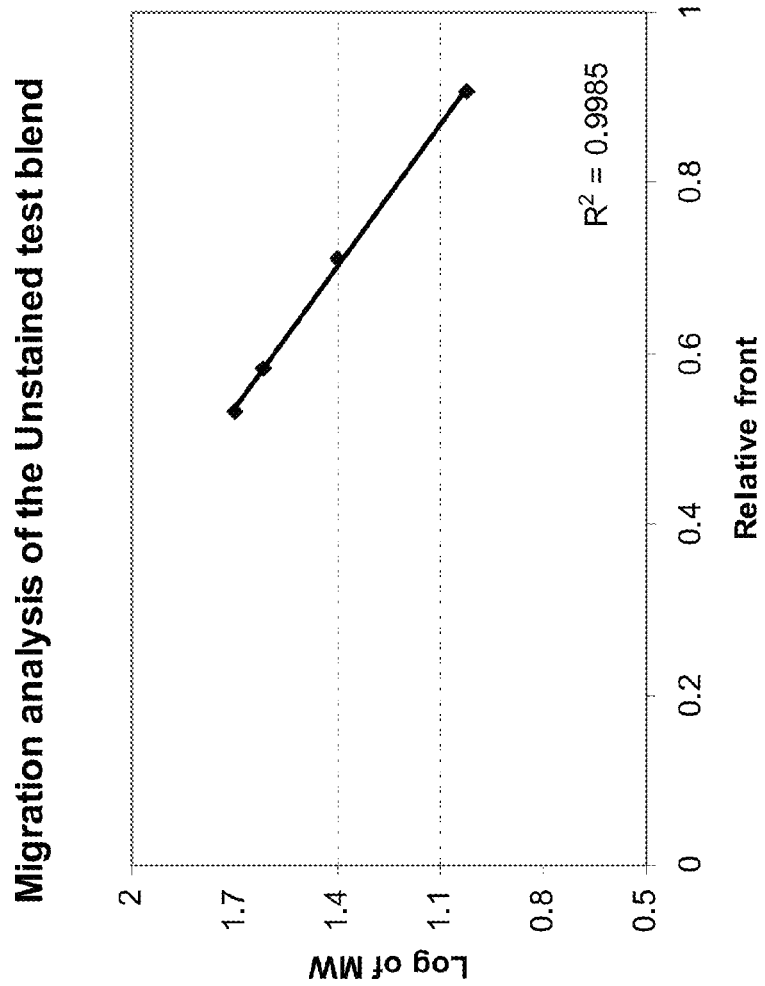
FIG. 7 provides an example of a test blend of purified proteins for making protein standards. The purified proteins were blended together with 1× Laemmli buffer. The blended protein standard in triplicate was separated on 4-20% Criterion Tris-HCl gels. The gel was fixed and stained with Bio-Safe before destaining and imaging by GS-800 densitometer. The relative front values were obtained using Quantity One software and plotted with Log of molecular weights of the four proteins.
Figure 7:
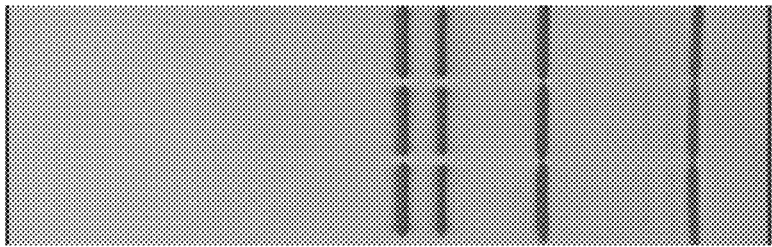

Purified physical analog were used to make proteins standards. Four reverse physical analog proteins, including Xrg1, Xrg2, and PBM, were blended together with 1× Laemmli buffer. The blended protein standard in triplicate was separated on 4-20% Criterion Tris-HCl gels. The gel was fixed and stained with Bio-Safe before destaining and imaging by GS-800 densitometer. The relative front values were obtained using Quantity One software and plotted with Log of molecular weights of the 4 proteins. The results (FIG. 7) demonstrated that physical analogs can be used as molecular weight markers.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled.

The disclosures of all articles and references, including patent applications and publications, are incorporated herein by reference for all purposes.

Examples of Sequences

```
BinB (3.4 kDa, pI 6.90) reference sequence
                                                      SEQ ID NO: 1
FVNQHLCGSH LVEALYLVCG ERGFFYTPKA BniB (3.4 kDa, pI 6.90, reversed BinB) physical analog sequence
                                                      SEQ ID NO: 2
AKPTYFFGRE GCVLYLAEVL HSGCLHQNVF Grx1 (10.51 kDa, pI 5.92) reference sequence (His6 (SEQ ID NO: 9)
tag underlined)
                                                      SEQ ID NO: 3
MQTVIFGRSG CPYCVRAKDL AEKLSNERDD FQYQYVDIRA EGITKEDLQQ KAGKPVETVP

QIFVDQQHIG GYTDFAAWVK ENLDAHHHHH H

Xrg1 (10.51 kDa, pI 5.92, reversed Grx1) physical analog sequence
(His6 (SEQ ID NO: 9) tag underlined)
                                                      SEQ ID NO: 4
MQADLNEKVW AAFDTYGGIH QQDVFIQPVT EVPKGAKQQL DEKTIGEARI DVYQYQFDDR

ENSLKEALDK ARVCYPCGSR GFIVTHHHHH H

Grx2 (25.17 kDa, pI 7.94) reference sequence (His6 (SEQ ID NO: 9)
tag underlined)
                                                      SEQ ID NO: 5
MKLYIYDHCP YCLKARMIFG LKNIPVELHV LLNDDAETPT RMVGQKQVPI LQKDDSRYMP

ESMDIVHYVD KLDGKPLLTG KRSPAIEEWL RKVNGYANKL LLPRFAKSAF DEFSTPAARK

YFVDKKEASA GNFADLLAHS DGLIKNISDD LRALDKLIVK PNAVNGELSE DDIQLFPLLR

NLTLVAGINW PSRVADYRDN MAKQTQINLL SSMAIHHHHH H

Xrg2 (25.17 kDa, pI 7.94, reversed Grx2) physical analog sequence
(His6 (SEQ ID NO: 9) tag underlined)
                                                      SEQ ID NO: 6
MKIAMSSLLN IQTQKAMNDR YDAVRSPWNI GAVLTLNRLL PFLQIDDESL EGNVANPKVI

LKDLARLDDS INKILGDSHA LLDAFNGASA EKKDVFYKRA APTSFEDFAS KAFRPLLLKN

AYGNVKRLWE EIAPSRKGTL LPKGDLKDVY HVIDMSEPMY RSDDKQLIPV QKQGVMRTPT

EADDNLLVHL EVPINKLGFI MRAKLCYPCH DYIYLHHHHH H

MBP (41.16 kDa, pI 5.48) reference sequence (His6 (SEQ ID NO: 9)
tag underlined)
                                                      SEQ ID NO: 7
MKIEEGKLVI WINGDKGYNG LAEVGKKFEK DTGIKVTVEH PDKLEEKFPQ VAATGDGPDI

IFWAHDRFGG YAQSGLLAEI TPDKAFQDKL YPFTWDAVRY NGKLIAYPIA VEALSLIYNK

DLLPNPPKTW EEIPALDKEL KAKGKSALMF NLQEPYFTWP LIAADGGYAF KYENGKYDIK

DVGVDNAGAK AGLTFLVDLI KNKHMNADTD YSIAEAAFNK GETAMTINGP WAWSNIDTSK

VNYGVTVLPT FKGQPSKPFV GVLSAGINAA SPNKELAKEF LENYLLTDEG LEAVNKDKPL

GAVALKSYEE ELAKDPRIAA TMENAQKGEI MPNIPQMSAF WYAVRTAVIN AASGRQTVDE

ALKDAQTHHH HHH

PBM (41.16 kDa, pI 5.48, reversed MBP) physical analog sequence
 (His6
(SEQ ID NO: 9) tag underlined)
                                                      SEQ ID NO: 8
MKTQADKLAE DVTQRGSAAN IVATRVAYWF ASMQPINPMI EGKQANEMTA AIRPDKALEE

EYSKLAVAGL PKDKNVAELG EDTLLYNELF EKALEKNPSA ANIGASLVGV FPKSPQGKFT

PLVTVGYNVK STDINSWAWP GNITMATEGK NFAAEAISYD TDANMHKNKI LDVLFTLGAK

AGANDVGVDK IDYKGNEYKF AYGGDAAILP WTFYPEQLNF MLASKGKAKL EKDLAPIEEW
```

-continued

TKPPNPLLDK NYILSLAEVA IPYAILKGNY RVADWTFPYL KDQFAKDPTI EALLGSQAYG

GFRDHAWFII DPGDGTAAVQ PFKEELKDPH EVTVKIGTDK EFKKGVEALG NYGKDGNIWI

VLKGEEIHHH HHH

---

What is claimed is:

1. A molecular weight marker composition that comprises an engineered polypeptide that comprises an amino acid sequence having at least 80% identity to an amino acid sequence set forth in SEQ ID NO:2, SEQ ID NO:4, SEQ ID NO:6, or SEQ ID NO:8; wherein the protein characterized by the amino acid sequence retains the same charge and molecular weight as a reference protein set forth in SEQ ID NO:1, SEQ ID NO:3, SEQ ID NO:5, or SEQ ID NO:7.

2. A method of determining the size of a protein present in a sample, the method comprising:
   electrophoresing the protein under denaturing conditions on a gel;
   electrophoresing on the same gel a molecular weight marker composition that comprises recombinant molecular weight marker proteins having molecular weights from about 10 to about 250 kDa wherein each of the molecular weight marker proteins in the composition is a purified protein and at least one of the molecular weight marker proteins is an engineered polypeptide comprising a physical analog of a naturally occurring reference protein amino acid sequence of at least 80 amino acids in length, wherein the reference protein is naturally occurring and wherein the analog: (i) is at least 80 amino acids in length and has the same amino acid composition as the reference protein sequence; (ii) has a primary sequence that has less than 50% identity to the reference protein sequence; and (iii) comprises a reversed sequence of at least 50 amino acids in length or a scrambled sequence of at least 50 amino acids in length, relative to the reference protein amino acid sequence; and
   comparing the size of the protein in the samples to the molecular weight markers present in the molecular weight marker composition, thereby determining the size of the protein present in the sample.

3. The method of claim 2, wherein the physical analog comprises a reversed sequence of at least 50 amino acids in length, relative to a reference protein sequence.

4. The method of claim 2, wherein the physical analog comprises a scrambled sequence of at least 50 amino acids in length, relative to a reference protein sequence.

5. The method of claim 2, wherein the engineered polypeptide comprises at least two repeated physical analog sequences.

6. The method of claim 2, wherein the molecular weight marker composition comprises at least a second engineered polypeptide comprising a physical analog.

7. The method of claim 2, wherein the molecular weight molecular weight marker composition comprises a recombinant molecular weight marker protein of about 3 kDa.

8. A molecular weight composition comprising an aqueous solution and prestained molecular weight marker proteins of different sizes to provide a range of molecular weights from about 10 to about 250 kDa, wherein each of the molecular weight marker proteins is purified and at least one of the molecular weight marker proteins is an engineered polypeptide comprising a physical analog of a reference protein amino acid sequence of at least 80 amino acids in length, wherein the reference protein amino acid sequence is selected from the group consisting of SEQ ID NO:3, SEQ ID NO:5, and SEQ ID NO:7; and wherein the analog: (i) is at least 80 amino acids in length and has the same amino acid composition as the reference protein sequence; (ii) has a primary sequence that has less than 50% identity to the reference protein sequence; and (iii) comprises a reversed sequence of at least 50 amino acids in length or a scrambled sequence of at least 50 amino acids in length, relative to the reference protein amino acid sequence.

9. The molecular weight composition of claim 8, wherein the physical analog has an amino acid sequence of SEQ ID NO:4, SEQ ID NO:6, or SEQ ID NO:8.

10. The method of claim 2, wherein the molecular weight marker proteins are pre-stained.

* * * * *

SEQUENCE LISTING

<160> NUMBER OF SEQ ID NOS: 12

<210> SEQ ID NO 1
<211> LENGTH: 30
<212> TYPE: PRT
<213> ORGANISM: Artificial Sequence
<220> FEATURE:
<223> OTHER INFORMATION: synthetic BinB (3.4 kDa, pI 6.90) reference sequence

<400> SEQUENCE: 1

```
Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Ala
            20                  25                  30
```

<210> SEQ ID NO 2
<211> LENGTH: 30
<212> TYPE: PRT
<213> ORGANISM: Artificial Sequence
<220> FEATURE:
<223> OTHER INFORMATION: synthetic BniB (3.4 kDa, pI 6.90, reversed BinB) physical analog sequence

<400> SEQUENCE: 2

```
Ala Lys Pro Thr Tyr Phe Phe Gly Arg Glu Gly Cys Val Leu Tyr Leu
 1               5                  10                  15

Ala Glu Val Leu His Ser Gly Cys Leu His Gln Asn Val Phe
            20                  25                  30
```

<210> SEQ ID NO 3
<211> LENGTH: 91
<212> TYPE: PRT
<213> ORGANISM: Artificial Sequence
<220> FEATURE:
<223> OTHER INFORMATION: synthetic Grx1 (10.51 kDa, pI 5.92) reference sequence with His tag

<400> SEQUENCE: 3

```
Met Gln Thr Val Ile Phe Gly Arg Ser Gly Cys Pro Tyr Cys Val Arg
 1               5                  10                  15

Ala Lys Asp Leu Ala Glu Lys Leu Ser Asn Glu Arg Asp Asp Phe Gln
            20                  25                  30

Tyr Gln Tyr Val Asp Ile Arg Ala Glu Gly Ile Thr Lys Glu Asp Leu
        35                  40                  45

Gln Gln Lys Ala Gly Lys Pro Val Glu Thr Val Pro Gln Ile Phe Val
    50                  55                  60

Asp Gln Gln His Ile Gly Gly Tyr Thr Asp Phe Ala Ala Trp Val Lys
65                  70                  75                  80

Glu Asn Leu Asp Ala His His His His His His
                85                  90
```

<210> SEQ ID NO 4
<211> LENGTH: 91
<212> TYPE: PRT
<213> ORGANISM: Artificial Sequence

```
<220> FEATURE:
<223> OTHER INFORMATION: synthetic Xrg1 (10.51 kDa, pI 5.92, reversed
      Grx1) physical analog sequence with His tag

<400> SEQUENCE: 4

Met Gln Ala Asp Leu Asn Glu Lys Val Trp Ala Ala Phe Asp Thr Tyr
 1               5                  10                  15

Gly Gly Ile His Gln Gln Asp Val Phe Ile Gln Pro Val Thr Glu Val
                20                  25                  30

Pro Lys Gly Ala Lys Gln Gln Leu Asp Glu Lys Thr Ile Gly Glu Ala
            35                  40                  45

Arg Ile Asp Val Tyr Gln Tyr Gln Phe Asp Arg Glu Asn Ser Leu
 50                  55                  60

Lys Glu Ala Leu Asp Lys Ala Arg Val Cys Tyr Pro Cys Gly Ser Arg
 65                  70                  75                  80

Gly Phe Ile Val Thr His His His His His
                    85                  90

<210> SEQ ID NO 5
<211> LENGTH: 221
<212> TYPE: PRT
<213> ORGANISM: Artificial Sequence
<220> FEATURE:
<223> OTHER INFORMATION: synthetic Grx2 (25.17 kDa, pI 7.94) reference
      sequence with His tag

<400> SEQUENCE: 5

Met Lys Leu Tyr Ile Tyr Asp His Cys Pro Tyr Cys Leu Lys Ala Arg
 1               5                  10                  15

Met Ile Phe Gly Leu Lys Asn Ile Pro Val Glu Leu His Val Leu Leu
                20                  25                  30

Asn Asp Asp Ala Glu Thr Pro Thr Arg Met Val Gly Gln Lys Gln Val
            35                  40                  45

Pro Ile Leu Gln Lys Asp Asp Ser Arg Tyr Met Pro Glu Ser Met Asp
 50                  55                  60

Ile Val His Tyr Val Asp Lys Leu Asp Gly Lys Pro Leu Leu Thr Gly
 65                  70                  75                  80

Lys Arg Ser Pro Ala Ile Glu Glu Trp Leu Arg Lys Val Asn Gly Tyr
                85                  90                  95

Ala Asn Lys Leu Leu Leu Pro Arg Phe Ala Lys Ser Ala Phe Asp Glu
            100                 105                 110

Phe Ser Thr Pro Ala Ala Arg Lys Tyr Phe Val Asp Lys Lys Glu Ala
        115                 120                 125

Ser Ala Gly Asn Phe Ala Asp Leu Leu Ala His Ser Asp Gly Leu Ile
    130                 135                 140

Lys Asn Ile Ser Asp Asp Leu Arg Ala Leu Asp Lys Leu Ile Val Lys
145                 150                 155                 160

Pro Asn Ala Val Asn Gly Glu Leu Ser Glu Asp Ile Gln Leu Phe
                165                 170                 175

Pro Leu Leu Arg Asn Leu Thr Leu Val Ala Gly Ile Asn Trp Pro Ser
            180                 185                 190

Arg Val Ala Asp Tyr Arg Asp Asn Met Ala Lys Gln Thr Gln Ile Asn
        195                 200                 205

Leu Leu Ser Ser Met Ala Ile His His His His His
    210                 215                 220

<210> SEQ ID NO 6
```

```
<211> LENGTH: 221
<212> TYPE: PRT
<213> ORGANISM: Artificial Sequence
<220> FEATURE:
<223> OTHER INFORMATION: synthetic Xrg2 (25.17 kDa, pI 7.94, reversed
      Grx2) physical analog sequence with His tag

<400> SEQUENCE: 6
```

| Met | Lys | Ile | Ala | Met | Ser | Ser | Leu | Leu | Asn | Ile | Gln | Thr | Gln | Lys | Ala |
|---|---|---|---|---|---|---|---|---|---|---|---|---|---|---|---|
| 1 | | | | 5 | | | | | 10 | | | | | 15 | |

| Met | Asn | Asp | Arg | Tyr | Asp | Ala | Val | Arg | Ser | Pro | Trp | Asn | Ile | Gly | Ala |
|---|---|---|---|---|---|---|---|---|---|---|---|---|---|---|---|
| | | | 20 | | | | | 25 | | | | | 30 | | |

| Val | Leu | Thr | Leu | Asn | Arg | Leu | Leu | Pro | Phe | Leu | Gln | Ile | Asp | Asp | Glu |
|---|---|---|---|---|---|---|---|---|---|---|---|---|---|---|---|
| | | 35 | | | | | 40 | | | | | 45 | | | |

| Ser | Leu | Glu | Gly | Asn | Val | Ala | Asn | Pro | Lys | Val | Ile | Leu | Lys | Asp | Leu |
|---|---|---|---|---|---|---|---|---|---|---|---|---|---|---|---|
| 50 | | | | | 55 | | | | | 60 | | | | | |

| Ala | Arg | Leu | Asp | Asp | Ser | Ile | Asn | Lys | Ile | Leu | Gly | Asp | Ser | His | Ala |
|---|---|---|---|---|---|---|---|---|---|---|---|---|---|---|---|
| 65 | | | | | 70 | | | | | 75 | | | | | 80 |

| Leu | Leu | Asp | Ala | Phe | Asn | Gly | Ala | Ser | Ala | Glu | Lys | Lys | Asp | Val | Phe |
|---|---|---|---|---|---|---|---|---|---|---|---|---|---|---|---|
| | | | | 85 | | | | | 90 | | | | | 95 | |

| Tyr | Lys | Arg | Ala | Ala | Pro | Thr | Ser | Phe | Glu | Asp | Phe | Ala | Ser | Lys | Ala |
|---|---|---|---|---|---|---|---|---|---|---|---|---|---|---|---|
| | | | 100 | | | | | 105 | | | | | 110 | | |

| Phe | Arg | Pro | Leu | Leu | Lys | Asn | Ala | Tyr | Gly | Asn | Val | Lys | Arg | Leu |
|---|---|---|---|---|---|---|---|---|---|---|---|---|---|---|
| | | 115 | | | | | 120 | | | | | 125 | | |

| Trp | Glu | Glu | Ile | Ala | Pro | Ser | Arg | Lys | Gly | Thr | Leu | Leu | Pro | Lys | Gly |
|---|---|---|---|---|---|---|---|---|---|---|---|---|---|---|---|
| | | 130 | | | | | 135 | | | | | 140 | | | |

| Asp | Leu | Lys | Asp | Val | Tyr | His | Val | Ile | Asp | Met | Ser | Glu | Pro | Met | Tyr |
|---|---|---|---|---|---|---|---|---|---|---|---|---|---|---|---|
| 145 | | | | | 150 | | | | | 155 | | | | | 160 |

| Arg | Ser | Asp | Asp | Lys | Gln | Leu | Ile | Pro | Val | Gln | Lys | Gln | Gly | Val | Met |
|---|---|---|---|---|---|---|---|---|---|---|---|---|---|---|---|
| | | | | 165 | | | | | 170 | | | | | 175 | |

| Arg | Thr | Pro | Thr | Glu | Ala | Asp | Asp | Asn | Leu | Leu | Val | His | Leu | Glu | Val |
|---|---|---|---|---|---|---|---|---|---|---|---|---|---|---|---|
| | | | 180 | | | | | 185 | | | | | 190 | | |

| Pro | Ile | Asn | Lys | Leu | Gly | Phe | Ile | Met | Arg | Ala | Lys | Leu | Cys | Tyr | Pro |
|---|---|---|---|---|---|---|---|---|---|---|---|---|---|---|---|
| | | 195 | | | | | 200 | | | | | 205 | | | |

| Cys | His | Asp | Tyr | Ile | Tyr | Leu | His | His | His | His | His |
|---|---|---|---|---|---|---|---|---|---|---|---|
| | 210 | | | | | 215 | | | | | 220 |

```
<210> SEQ ID NO 7
<211> LENGTH: 373
<212> TYPE: PRT
<213> ORGANISM: Artificial Sequence
<220> FEATURE:
<223> OTHER INFORMATION: synthetic MBP (41.16 kDa, pI 5.48) reference
      sequence with His tag

<400> SEQUENCE: 7
```

| Met | Lys | Ile | Glu | Glu | Gly | Lys | Leu | Val | Ile | Trp | Ile | Asn | Gly | Asp | Lys |
|---|---|---|---|---|---|---|---|---|---|---|---|---|---|---|---|
| 1 | | | | 5 | | | | | 10 | | | | | 15 | |

| Gly | Tyr | Asn | Gly | Leu | Ala | Glu | Val | Gly | Lys | Lys | Phe | Glu | Lys | Asp | Thr |
|---|---|---|---|---|---|---|---|---|---|---|---|---|---|---|---|
| | | | 20 | | | | | 25 | | | | | 30 | | |

| Gly | Ile | Lys | Val | Thr | Val | Glu | His | Pro | Asp | Lys | Leu | Glu | Glu | Lys | Phe |
|---|---|---|---|---|---|---|---|---|---|---|---|---|---|---|---|
| | | 35 | | | | | 40 | | | | | 45 | | | |

| Pro | Gln | Val | Ala | Ala | Thr | Gly | Asp | Gly | Pro | Asp | Ile | Ile | Phe | Trp | Ala |
|---|---|---|---|---|---|---|---|---|---|---|---|---|---|---|---|
| 50 | | | | | 55 | | | | | 60 | | | | | |

| His | Asp | Arg | Phe | Gly | Gly | Tyr | Ala | Gln | Ser | Gly | Leu | Leu | Ala | Glu | Ile |
|---|---|---|---|---|---|---|---|---|---|---|---|---|---|---|---|
| 65 | | | | | 70 | | | | | 75 | | | | | 80 |

| Thr | Pro | Asp | Lys | Ala | Phe | Gln | Asp | Lys | Leu | Tyr | Pro | Phe | Thr | Trp | Asp |
|---|---|---|---|---|---|---|---|---|---|---|---|---|---|---|---|
| | | | | 85 | | | | | 90 | | | | | 95 | |

```
Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
            165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
            245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
            325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr His
            355                 360                 365

His His His His His
    370

<210> SEQ ID NO 8
<211> LENGTH: 373
<212> TYPE: PRT
<213> ORGANISM: Artificial Sequence
<220> FEATURE:
<223> OTHER INFORMATION: synthetic PBM (41.16 kDa, pI 5.48, reversed
      MBP) physical analog sequence with His tag

<400> SEQUENCE: 8

Met Lys Thr Gln Ala Asp Lys Leu Ala Glu Asp Val Thr Gln Arg Gly
  1               5                  10                  15

Ser Ala Ala Asn Ile Val Ala Thr Arg Val Ala Tyr Trp Phe Ala Ser
             20                  25                  30

Met Gln Pro Ile Asn Pro Met Ile Glu Gly Lys Gln Ala Asn Glu Met
             35                  40                  45

Thr Ala Ala Ile Arg Pro Asp Lys Ala Leu Glu Glu Glu Tyr Ser Lys
 50                  55                  60

Leu Ala Val Ala Gly Leu Pro Lys Asp Lys Asn Val Ala Glu Leu Gly
```

```
              65                  70                  75                  80
        Glu Asp Thr Leu Leu Tyr Asn Glu Leu Phe Glu Lys Ala Leu Glu Lys
                            85                  90                  95

Asn Pro Ser Ala Ala Asn Ile Gly Ala Ser Leu Val Gly Val Phe Pro
                        100                 105                 110

Lys Ser Pro Gln Gly Lys Phe Thr Pro Leu Val Thr Val Gly Tyr Asn
                        115                 120                 125

Val Lys Ser Thr Asp Ile Asn Ser Trp Ala Trp Pro Gly Asn Ile Thr
                    130                 135                 140

Met Ala Thr Glu Gly Lys Asn Phe Ala Ala Glu Ala Ile Ser Tyr Asp
        145                 150                 155                 160

Thr Asp Ala Asn Met His Lys Asn Lys Ile Leu Asp Val Leu Phe Thr
                            165                 170                 175

Leu Gly Ala Lys Ala Gly Ala Asn Asp Val Gly Val Asp Lys Ile Asp
                        180                 185                 190

Tyr Lys Gly Asn Glu Tyr Lys Phe Ala Tyr Gly Gly Asp Ala Ala Ile
                        195                 200                 205

Leu Pro Trp Thr Phe Tyr Pro Glu Gln Leu Asn Phe Met Leu Ala Ser
                    210                 215                 220

Lys Gly Lys Ala Lys Leu Glu Lys Asp Leu Ala Pro Ile Glu Glu Trp
        225                 230                 235                 240

Thr Lys Pro Pro Asn Pro Leu Leu Asp Lys Asn Tyr Ile Leu Ser Leu
                            245                 250                 255

Ala Glu Val Ala Ile Pro Tyr Ala Ile Leu Lys Gly Asn Tyr Arg Val
                        260                 265                 270

Ala Asp Trp Thr Phe Pro Tyr Leu Lys Asp Gln Phe Ala Lys Asp Pro
                        275                 280                 285

Thr Ile Glu Ala Leu Leu Gly Ser Gln Ala Tyr Gly Gly Phe Arg Asp
                    290                 295                 300

His Ala Trp Phe Ile Ile Asp Pro Gly Asp Gly Thr Ala Ala Val Gln
        305                 310                 315                 320

Pro Phe Lys Glu Glu Leu Lys Asp Pro His Glu Val Thr Val Lys Ile
                            325                 330                 335

Gly Thr Asp Lys Glu Phe Lys Lys Gly Val Glu Ala Leu Gly Asn Tyr
                        340                 345                 350

Gly Lys Asp Gly Asn Ile Trp Ile Val Leu Lys Gly Glu Glu Ile His
                        355                 360                 365

His His His His His
                370

<210> SEQ ID NO 9
<211> LENGTH: 6
<212> TYPE: PRT
<213> ORGANISM: Artificial Sequence
<220> FEATURE:
<223> OTHER INFORMATION: synthetic His tag, His6 tag, poly-His

<400> SEQUENCE: 9

His His His His His His
 1               5

<210> SEQ ID NO 10
<211> LENGTH: 5
<212> TYPE: PRT
<213> ORGANISM: Artificial Sequence
<220> FEATURE:
<223> OTHER INFORMATION: synthetic glycine-serine polymer, peptide
```

```
                linker, spacer
<220> FEATURE:
<221> NAME/KEY: REPEAT
<222> LOCATION: (1)...(5)
<223> OTHER INFORMATION: linker (GGGGS)-n, where n is at least one,
      present an undefined number of times

<400> SEQUENCE: 10

Gly Gly Gly Gly Ser
 1               5

<210> SEQ ID NO 11
<211> LENGTH: 5
<212> TYPE: PRT
<213> ORGANISM: Artificial Sequence
<220> FEATURE:
<223> OTHER INFORMATION: synthetic glycine-serine polymer, peptide
      linker, spacer
<220> FEATURE:
<221> NAME/KEY: REPEAT
<222> LOCATION: (1)...(5)
<223> OTHER INFORMATION: linker (GSGGS)-n, where n is at least one,
      present an undefined number of times

<400> SEQUENCE: 11

Gly Ser Gly Gly Ser
 1               5

<210> SEQ ID NO 12
<211> LENGTH: 4
<212> TYPE: PRT
<213> ORGANISM: Artificial Sequence
<220> FEATURE:
<223> OTHER INFORMATION: synthetic glycine-serine polymer, peptide
      linker, spacer
<220> FEATURE:
<221> NAME/KEY: REPEAT
<222> LOCATION: (1)...(4)
<223> OTHER INFORMATION: linker (GGGS)-n, where n is at least one,
      present an undefined number of times

<400> SEQUENCE: 12

Gly Gly Gly Ser
 1
```